United States Patent
Lakhotia et al.

(10) Patent No.: US 9,267,929 B2
(45) Date of Patent: *Feb. 23, 2016

(54) TECHNIQUES FOR CALCULATING GAS CONCENTRATIONS IN A FLUID ENVIRONMENT

(75) Inventors: Vikas Lakhotia, Valencia, CA (US); G. Jordan Maclay, Richland Center, WI (US)

(73) Assignee: H2Scan Corporation, Valencia, CA (US)

( * ) Notice: Subject to any disclaimer, the term of this patent is extended or adjusted under 35 U.S.C. 154(b) by 769 days.

This patent is subject to a terminal disclaimer.

(21) Appl. No.: 13/607,079

(22) Filed: Sep. 7, 2012

(65) Prior Publication Data

US 2013/0086975 A1   Apr. 11, 2013

Related U.S. Application Data

(63) Continuation of application No. 13/269,368, filed on Oct. 7, 2011, now Pat. No. 8,265,881.

(51) Int. Cl.
*G01N 27/12* (2006.01)
*G01N 33/00* (2006.01)

(52) U.S. Cl.
CPC ............ *G01N 33/005* (2013.01); *G01N 27/123* (2013.01); *G01N 33/0059* (2013.01)

(58) Field of Classification Search
CPC ........................... G01N 27/123; G01N 33/005
See application file for complete search history.

(56) References Cited

U.S. PATENT DOCUMENTS

| | | |
|---|---|---|
| 4,902,138 A | 2/1990 | Goeldner et al. |
| 5,279,795 A | 1/1994 | Hughes et al. |
| 2006/0042965 A1 | 3/2006 | Sasaki et al. |
| 2009/0126454 A1 | 5/2009 | Pratt et al. |
| 2009/0133472 A1 | 5/2009 | Tada et al. |
| 2010/0033214 A1 | 2/2010 | Deshpande et al. |

(Continued)

FOREIGN PATENT DOCUMENTS

| | | |
|---|---|---|
| DE | 10003676 A1 | 8/2001 |
| EP | 0878703 A2 | 11/1998 |

(Continued)

OTHER PUBLICATIONS

PCT, Notification Concerning Transmittal of International Preliminary Report on Patentability, in Application No. PCT/US2012/058834, dated Apr. 17, 2014 (8 pages).

(Continued)

*Primary Examiner* — Harshad R Patel
*Assistant Examiner* — Punam Roy
(74) *Attorney, Agent, or Firm* — Leech Tishman Fuscaldo & Lampl (57) ABSTRACT

A method can be performed by adjusting a temperature of a gas sensor to a first temperature value for a first period of time and a second temperature value for a second period of time. The gas sensor signal may be measured during the first period of time to determine a first signal value and during the second period of time to determine a second value. Then, concentration information for at least one gas is calculated according to the first signal value and the second signal value. While the gas sensor signal may include information about a presence of a first gas and a second gas, the concentration information for the at least one gas may not substantially include concentration information for the second gas.

24 Claims, 9 Drawing Sheets

(56) References Cited

U.S. PATENT DOCUMENTS

2010/0122568 A1     5/2010    Inoue et al.
2010/0332147 A1    12/2010    Stephens

FOREIGN PATENT DOCUMENTS

| KR | 10-0736831 | 7/2007 |
| KR | 10-2010-0096610 | 9/2010 |
| KR | 10-2011-0100674 | 9/2011 |
| WO | WO 85/01351 | 3/1985 |
| WO | WO 2010103401 A1 * | 9/2010 |

OTHER PUBLICATIONS

Maclay, G. Jordan, et al., Use of Time-dependent Chemical Sensor Signals for Selective Identification, Sensors and Actuators, 20 (1989), pp. 277-285.

Johansson, M., et al., "Bridging the pressure gap for palladium metal-insulator-semiconductor hydrogen sensors in oxygen containing environments," Department of Physics and Measurement Technology, Linkoping University, Sweden, Journal of Applied Physics, vol. 84, No. 1, Jul. 1, 1998.

Hughes, R.C., et al., "Solid-State Hydrogen Sensors Using Palladium-Nickel Alloys: Effect of Alloy Composition on Sensor Response," Sandia National Laboratories, Alburquerque, New Mexico, J. Electrochemical Soc., vol. 142, No. 1, Jan. 1995.

Patent Cooperation Treaty, Notification of Transmittal of the International Search Report and the Written Opinion of the International Searching Authority, or the Declaration, in International application No. PCT/US12/58834, dated Oct. 23, 2012.

Korean Intellectual Property Office, Preliminary Rejection issued in Korean Patent Application No. 10-2014-7012344, Aug. 27, 2014, 13 pages.

A. Burresi, et al., "Dynamic CO Recognition in Presence of Interfering Gases by Using One MOX Sensor and a Selected Temperature Profile," Sensors and Actuators B: Chemical: International Journal Devoted to Research and Development of Physical and Chemical Transducers, Elsevier S.A. CH, vol. 106, No. 1, Apr. 29, 2005, pp. 40-43.

European Patent Office, Extended European Search Report issued in European Patent Application No. 12838781.8, Jul. 23, 2015, 10 pages.

* cited by examiner

Prior Art

TECHNIQUES FOR CALCULATING GAS CONCENTRATIONS IN A FLUID ENVIRONMENT

CROSS REFERENCE TO RELATED APPLICATIONS

This application is a continuation of U.S. patent application Ser. No. 13/269,368 filed on Oct. 7, 2011 and issued as U.S. Pat. No. 8,265,881, the entirety of which is herein incorporated by reference.

FEDERALLY SPONSORED RESEARCH OR DEVELOPMENT

Not Applicable

JOINT RESEARCH AGREEMENT

Not Applicable

SEQUENCE LISTING

Not Applicable

BACKGROUND OF THE APPLICATION

Generally speaking, this application discloses techniques of measuring concentration information for one or more gasses in a fluid environment with gas sensors.

Gas sensors may be sensitive to a partial pressure or concentration of one or more gasses in a fluid environment. Some types of gas sensors may include those described in U.S. Pat. No. 5,279,795 or U.S. Patent Publication No. 2010/033214. Such sensors may be sensitive to one or more types of gas such as $H_2$ or $O_2$. Gas sensors may be designed to provide measurements from which a gas pressure can be estimated. Such measurements may correspond to variations in resistance and/or capacitance of a gas sensor in response to changing concentrations of gasses. A gas sensor may include palladium, such as a palladium-nickel alloy or a palladium metal-oxide semiconductor. Some mechanisms of resistance and capacitance variations in gas sensors are explained in Bridging the Pressure Gap for Palladium Metal-Insulator-Semiconductor Hydrogen Sensors in Oxygen Containing Environments, M. Johansson et al., Journal of Applied Physics, Vol. 84, July 1998 and R. C. Hughes et al., Solid-State Hydrogen Sensors Using Palladium-Nickel Alloys: Effect of Alloy Composition on Sensor Response, J. Electrochem. Soc., Vol. 142, No. 1, January 1995. It should be emphasized that the techniques disclosed in this application are in no way limited to such gas sensor structures or physical mechanisms.

Some gas sensors, such one that has a PdNi lattice, may have increased resistance or capacitance as concentration information for $H_2$ increases. For example, resistance may increase linearly in proportion to the levels of hydrogen in a PdNi lattice, which in turn is related to gaseous $H_2$ pressure as described by Sievert's law. This law holds that, at moderate pressures, concentration for hydrogen dissolved in solid metals is approximated by the following relationship:

$$c \approx s * p^{1/2}$$

where c is the concentration of dissolved hydrogen in equilibrium with gaseous hydrogen at pressure p, and s is Sievert's parameter.

For a given application, a gas sensing system can be designed to detect the pressure of a target gas, for example, $H_2$. In addition to the target gas pressure, however, there may be factors that can influence a gas sensor's measurements. For example, temperature of the gas sensor may influence measurements. To address this issue, a heater may be used to maintain the gas sensor within a desired temperature range. In addition to temperature, other factors may influence gas sensor measurements, such as a bias voltage applied to the gas sensor or the overall pressure of the fluid environment.

As another example, non-target gasses, such as $O_2$, may influence a gas sensor's measurements. The presence of non-target gasses may influence or interfere with target gas measurements in at least two ways. First, because the sensor is responding to both a target and a non-target gas, the sensor reading may be too high or too low. In this respect, the influence of the non-target gas may be thought of as an offset to the target gas reading. Second, the presence of a non-target gas can alter the way a sensor measures a target gas. For example, non-target gasses can occupy receptor sites inside or on the surface of the lattice. This leaves less available receptor sites, thereby making the sensor less sensitive to the target-gas. As another example, in a PdNi gas sensor, the presence of oxygen in the lattice may affect the resistive or capacitive characteristics of the sensor. Thus, an oxygen-permeated lattice may respond to the presence of hydrogen in a different way than if the lattice was not permeated with oxygen. When oxygen permeates the lattice adsorption of hydrogen results in the formation of molecules such as $H_2O$, OH, etc. These molecules may, by themselves, influence the resistive or capacitive characteristics of the gas sensor.

One attempted solution for reducing the influence of non-target gasses may be to use a blocking coating on a gas sensor to filter such non-target gasses. However, such a filter may reduce a gas sensor's sensitivity or response time. Another attempted solution may be to use multiple gas sensors to specifically detect non-target gasses to determine and account for concentration information for non-target gasses. However, such a solution may be expensive and/or introduce additional system complexity. Yet another attempted solution is to simply limit gas sensing applications to ones that do not include interfering gasses.

As another example of gas sensor influences, the character of a gas sensor tends to change over time, thus causing "drift." One solution to such a problem is to repeatedly recalibrate a drifting sensor manually.

In view of the foregoing, it may be useful to provide a gas sensing system that reduces the effects of interferences with the gas sensor measurements of a target gas.

BRIEF SUMMARY OF THE APPLICATION

According to embodiments of the present application, a system includes a sensing unit that has a gas sensor and a heater. The gas sensor generates a gas sensor signal in response to a presence of at least one gas. The heater adjusts a temperature of the sensor.

The system also includes at least one processor, which controls the heater to adjust the temperature of the sensor to a first temperature value for a first period of time and determine a first signal value by measuring the gas sensor signal or change in the gas sensor signal with time during the first period of time. The first signal value may be measured at approximately the end of the first period of time.

The processor controls the heater to adjust the temperature of the sensor to a second temperature value for a second period of time and determine a second signal value by measuring the gas sensor signal or change in the gas sensor signal with time during the second period of time. The first and second temperature values are different (for example, 50° C. and 90° C.). The second signal value may be measured at approximately the end of the second period of time.

Additionally, the processor calculates concentration information for at least one gas according to the first signal value and the second signal value. The calculation may also be made according to a first calibration relationship of the sensing unit at the first temperature as well as a second calibration relationship of the sensing unit at the second temperature. While the gas sensor may respond to a presence of a first gas and a second gas, the concentration information for the at least one gas does not substantially include concentration information for the second gas. In an embodiment, the first gas is $H_2$ and the second gas is $O_2$.

The system may also include an additional sensing unit that also has a gas sensor and a heater. In such an embodiment, the processor may be adapted to control the heater of the additional sensing unit to adjust the temperature of the additional sensing unit to a third temperature value during both the first period of time and the second period of time. The first and third temperature values may be substantially the same. The processor also determines a sequence of varying signal values by measuring the additional gas sensor signal periodically throughout the first period of time and the second period of time. Additionally, the processor calculates concentration information for the at least one gas according to the first signal value, the second signal value, and the varying signal values.

According to embodiments of the present application, a method can be performed by adjusting a temperature of a gas sensor to a first temperature value (for example, 50° C.) for a first period of time and a second temperature value (for example, 90° C.) for a second period of time. The gas sensor signal may be measured during the first period of time to determine a first signal value and during the second period of time to determine a second value. These measurements may be made at approximately the ends of the periods of time. Then, concentration information for at least one gas is calculated according to the first signal value and the second signal value. While the gas sensor signal may include information about a presence of a first gas (for example, $H_2$) and a second gas (for example, $O_2$), the concentration information for the at least one gas may not substantially include concentration information for the second gas. In an embodiment, concentration information is calculated according to calibration relationships of the gas sensor at the first and second temperature values.

The method may also be performed by adjusting a temperature of an additional gas sensor to a third temperature value (for example, the same as the first temperature value) during the first period of time or the second period of time. A sequence of varying signal values can be determined by measuring a signal from the additional gas sensor periodically throughout the first and second periods of time. Additionally, concentration information for the at least one gas may be determined according to the first signal value, the second signal value, and the varying signal values. Note, that this method (and various embodiments thereof) may be performed by one or more processors executing a set of instructions stored on a computer-readable medium.

According to embodiments of the present application, a method can be performed by creating two different states for at least one of a sensing unit or a target environment. The first state is created over a first period of time and the second state is created over a second period of time. A signal of the sensing unit is measured during the first and second periods of time to determine respective first and second values of the signal. Concentration information for at least one gas in the target environment is calculated according to the first and second signal values. For example, the states may be different temperature values of a gas sensor in the sensing unit, different bias voltages of the gas sensor, and/or different pressures of the target environment. The target environment may include a first gas (for example, $H_2$) and a second gas (for example, $O_2$). While the first and second signal values may include information about concentrations of the first and second gasses, the method may provide a way to determine concentration information for the at least one gas that does not substantially include concentration information for the second gas.

In an embodiment, the sensing unit is calibrated in the first state and in the second state to form calibration relationships. Concentration information for the at least one gas is then calculated according to the first and second values of the signal and the calibration relationships.

Note, that this method (and various embodiments thereof) may be performed by one or more processors executing a set of instructions stored on a computer-readable medium.

The foregoing summary, as well as the following detailed description of certain embodiments of the present application, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE APPLICATION

Figure 1:
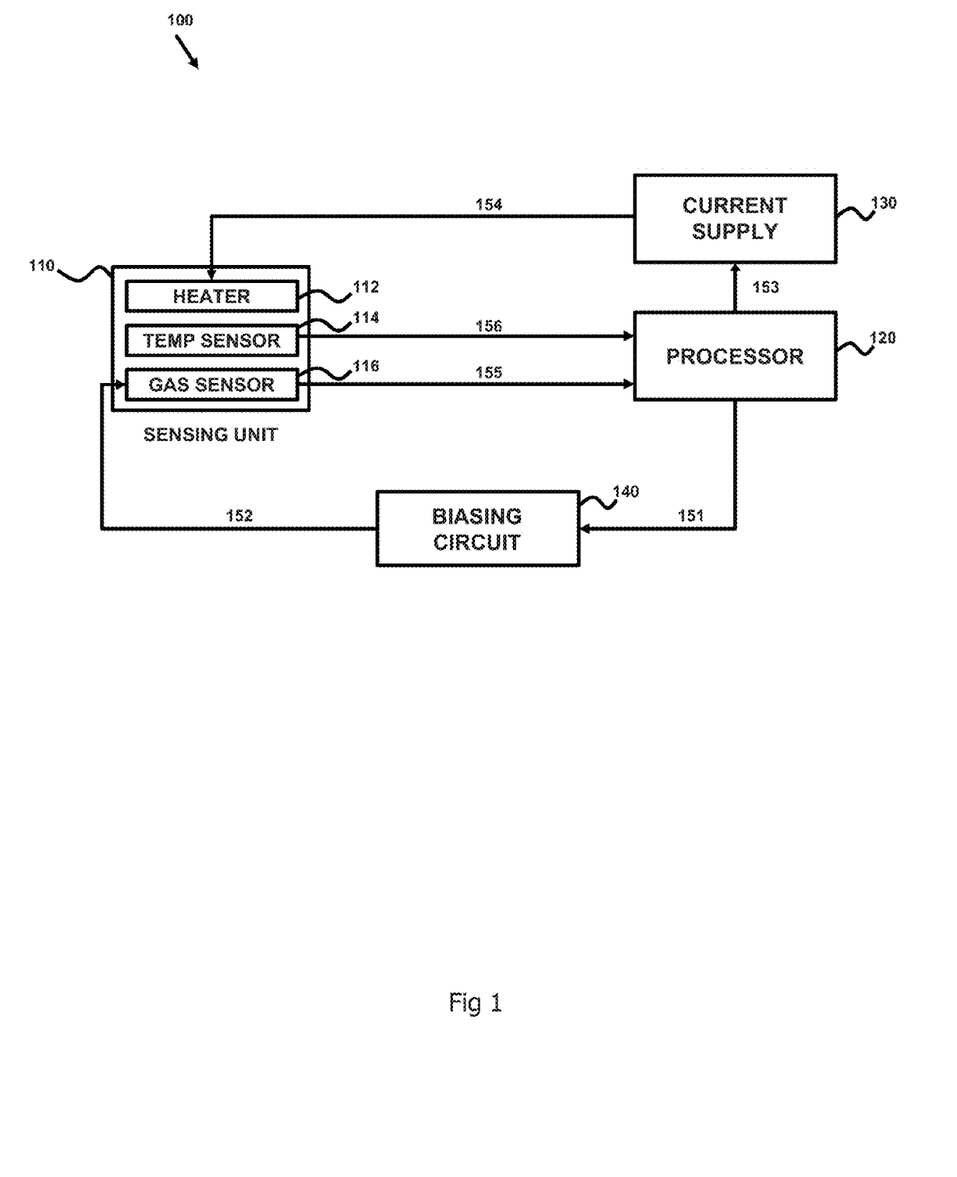
FIG. 1 shows a gas sensing system, according to an embodiment of the present application.

FIG. 1 shows a gas sensing system 100, according to an embodiment of the present application. The system 100 may include a sensing unit 110, a processor 120, a current supply 130, and a biasing circuit 140. The sensing unit 110 may include a heater 112, a temperature sensor 114, and a gas sensor 116.

The processor 120 may communicate a signal 153 to the current supply 130. In response to the signal 153, the current supply 130 may deliver an appropriate current to the heater 112 through the conductor 154. The processor 120 may also communicate a signal 151 to the biasing circuit. In response to the signal 151, the biasing circuit may apply an appropriate bias voltage to the gas sensor 116.

The processor 120 may include sub-processing portions, such as a digital signal processor. The processor 120 may be capable of executing a set of instructions from a computer-readable medium that effects gas measurement methods, such as the ones shown in FIGS. 5-6 and described below. The processor 120 may receive input data from a user interface (not shown), and may provide displayable data to a display (not shown).

The heater 112 may be capable of controlling the temperature of a sensing environment including the gas sensor 116. The heater 112 may be a resistive heater. The heater 112 may be employed by the processor 120 to control the temperature of a substrate in the gas sensor 116 by controlling the current flowing through the heater in a closed-loop with the temperature sensor 114.

The gas sensor 116 may sense the presence of one or more gasses in a fluid environment and communicate concentration information corresponding to concentration(s) of the one or more gasses to the processor 120. It should be understood that the term "concentration information" may refer to any information that may be used to infer or estimate concentration(s) of one or more gasses in a target environment. For example, "concentration information" may include partial pressure information or changes in optical properties information.

A fluid environment may include a mixed atmosphere that has one or more gasses with variable concentrations. These gasses may include, for example, $H_2$ and $O_2$. The mixed atmosphere may also include other constituent gasses, such as $H_2O$, $CO$, $H_2S$, $Cl_2$, and $N_2$. A fluid environment may also include a liquid with dissolved gasses, such as the ones listed above.

Figure 2:
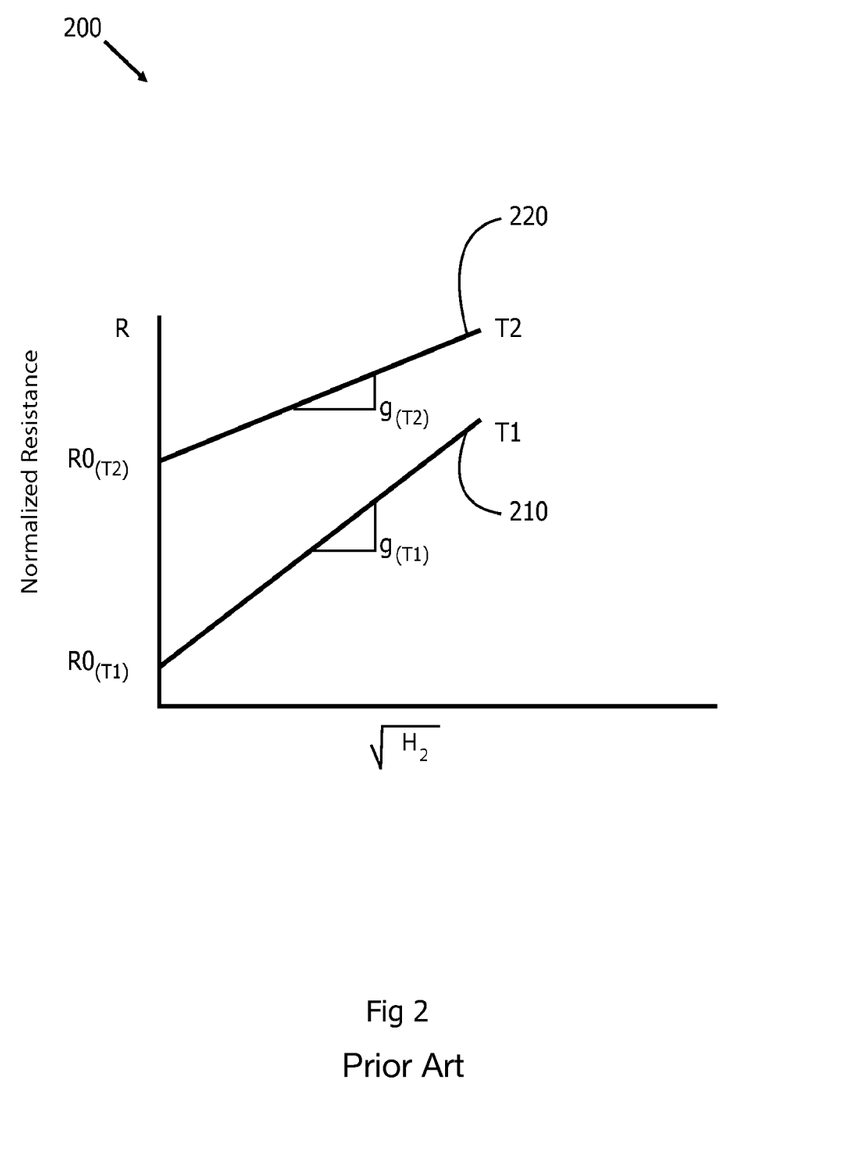
FIG. 2 shows a graph showing relationships between $H_2$ concentration information in a fluid environment and a resistance of a gas sensor, according to an embodiment of the information for $H_2$ as calculated by information from a gas sensing system over a period of time, according to the prior art.

FIGS. 2-3 are illustrative examples of techniques to detect concentration information for $H_2$ in a mixed gaseous atmosphere. These examples are illustrative only, and a target gas could be other molecules/atoms, such as $O_2$. These techniques measure variable resistances in one or more gas sensors, but other properties may be measured, such as capacitance of the gas sensor. These techniques may be implemented with a gas sensing system, such as system 100.

FIG. 2 shows a graph 200 showing relationships between $H_2$ concentration information in a fluid environment and a resistance of a gas sensor, according to an embodiment of the present application. The gas sensing system may be similar to the one illustrated in FIG. 1.

A first relationship 210 and a second relationship 220 are determined by exposing the gas sensor to varying concentrations of $H_2$ and measuring the resulting resistance of the gas sensor. The first relationship 210 may be determined while the gas sensor has a temperature of T1. The second relationship 220 may be determined while the gas sensor has a temperature of T2. The relationships 210 and 220 shown in graph 200 are illustrated according to the square root of the $H_2$ concentration information in the fluid environment versus the corresponding normalized resistance of the gas sensor. T1 may be, for example, approximately 50° C. T2 may be, for example, approximately 90° C. T1 and T2 could, of course, be other temperatures, such as 40°/80° C., 40°/90° C., 50°/80° C., etc. Therefore, the example of 50°/90° C. is just one of numerous examples. The relationships 210 and 220 may be linear (as shown in graph 200), may be polynomial equations of various degrees, or may have some other relationship. Also, note that certain embodiments may use multiple sensors. In such cases, relationships (similar to 210 and 220) may be determined for multiple sensors.

Once the calibration relationships have been determined, concentration information for $H_2$ may be obtained as follows. The gas sensor resistance may be measured and normalized. If the gas sensor has a temperature of T1, then the relationship 210 may be used. The shape of the relationship 210 may determine a corresponding square root of $H_2$ concentration information. This value may be squared, and the resulting $H_2$ concentration information may be determined. A similar process may be used with relationship 220 when the temperature of the gas sensor is T2. Note that the relationships 210 and 220 may be determined under virtually ideal circumstances without any substantially interferences, such as the presence of non-target gasses (for example, $O_2$) and the long-term effects of sensor drift. When a calibrated gas sensor is used in a "real-world" situation, the resulting calculations of $H_2$ may be inaccurate due to these and/or other interferences.

Figure 3A:
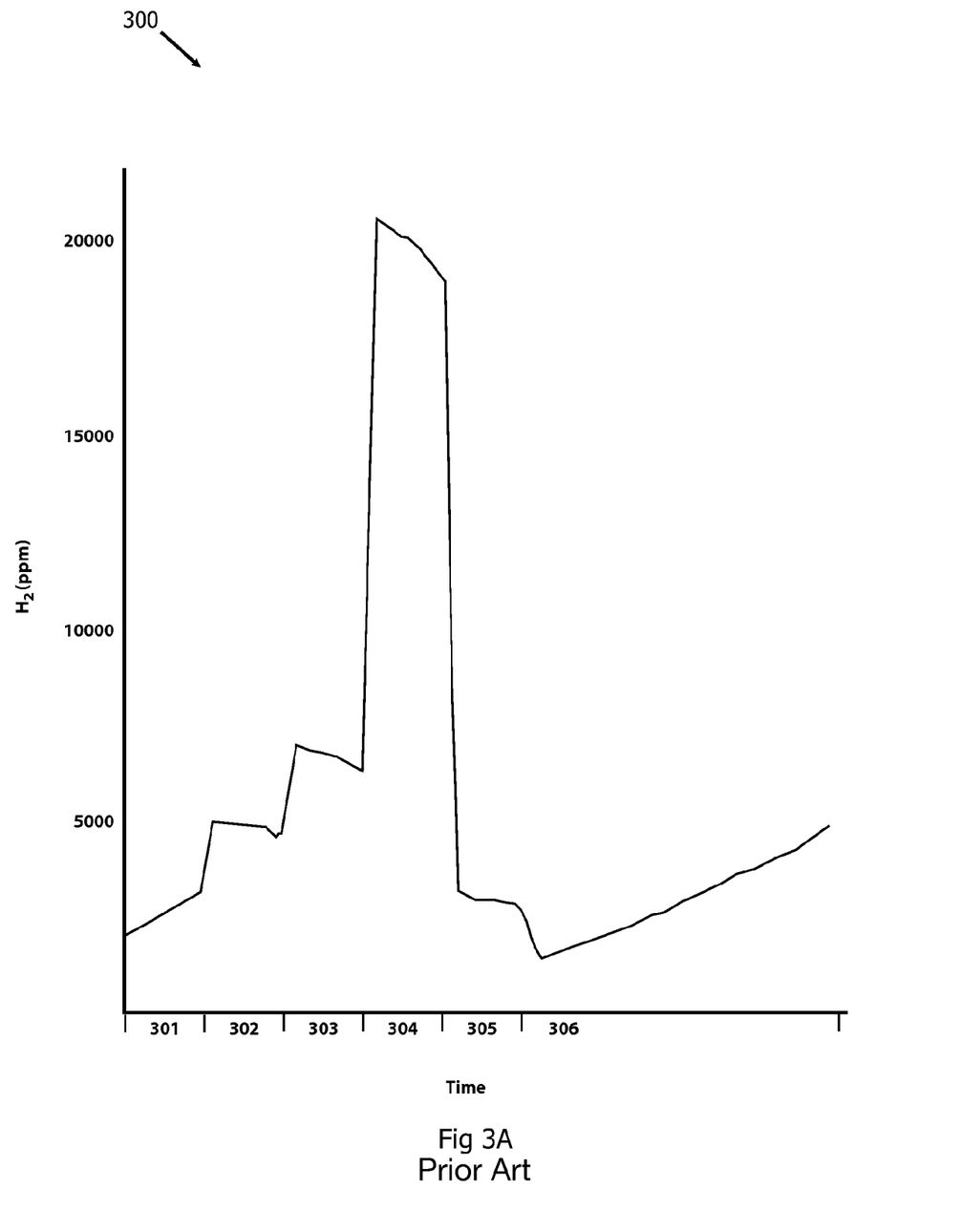
FIG. 3A shows a graph corresponding to measurements of a gas sensor over a period of time.

FIG. 3A shows a graph 300 of concentration information for $H_2$ as calculated by information from a gas sensor over time, according to the prior art. Throughout the duration of the six segments, the gas sensor may be maintained at a constant temperature, such as 50° C. The $H_2$ concentration information is shown in parts per million ("ppm"). Note, the $H_2$ concentration information is shown without any compensation for interferences. The time is shown as divided into six segments 301-306. The segments may be of arbitrary length and number and are depicted and described for illustrative purposes only. The gas sensor is exposed to different mixed atmospheres over the six time segments as shown in Table 1.

TABLE 1

| Time segment | Atmosphere composition |
| --- | --- |
| 301 | $O_2$ - 21% |
|  | $H_2$ - 0 ppm |
| 302 | $O_2$ - 0% |
|  | $H_2$ - 300 ppm |
| 303 | $O_2$ - 0% |
|  | $H_2$ - 1,000 ppm |
| 304 | $O_2$ - 0% |
|  | $H_2$ - 10,000 ppm |
| 305 | $O_2$ - 0% |
|  | $H_2$ - 300 ppm |
| 306 | $O_2$ - 21% |
|  | $H_2$ - 0 ppm |

Comparing FIG. 3A to Table 1, various observations can be made. For example, one can see that the gas sensor indicates inflated $H_2$ concentration information readings in FIG. 3A. Even during segments 301 and 306, when $H_2$ concentration information is 0 ppm, the gas sensor indicates $H_2$ concentration information as high as ~5,000 ppm. Furthermore, during segments 301 and 306, the apparent $H_2$ concentration ramps up. These anomalies may be a result of the presence of oxygen in the gas sensor. First, the presence of oxygen may cause a response in the gas sensor. Second, because it may take a relatively long time for the gas sensor to stabilize when exposed to a given $O_2$ concentration, the gas sensor may respond with a relatively slow increase in resistance, thereby causing the ramping anomaly.

As another observation, the apparent $H_2$ concentrations in FIG. 3A are higher than the actual $H_2$ concentrations. This may be a result of interference from oxygen causing, for example, an offset or changing the characteristics of the gas sensor's responsiveness to $H_2$ concentrations.

As another observation, in each of segments 302, 303, 304, and 305, the apparent concentration of $H_2$ tails off. This may be an effect of the dissipation of oxygen from the gas sensor. Without the presence of $O_2$ in the atmosphere, the oxygen in the gas sensor lattice may slowly be purged. This may occur slowly due to the relatively long stabilization periods of the gas sensor to oxygen as discussed above. As the oxygen dissipates, the influence of the oxygen on the gas sensor may be reduced. For example, while the $H_2$ concentration is 300 ppm during both segments 302 and 305, the measured $H_2$ is less inflated during segment 305 than during segment 302. This may be a result of less oxygen in the gas sensor. Note that the rate of the dissipation of oxygen may increase in response to increasing amounts of hydrogen. This may be observed by increased decay during segments of higher $H_2$ concentrations (for example, segments 303 and 304).

In addition to the aforementioned observations, other factors may be influencing the apparent $H_2$ readings, such as drift in the gas sensor and the presence of other non-target gasses.

Figure 3B:
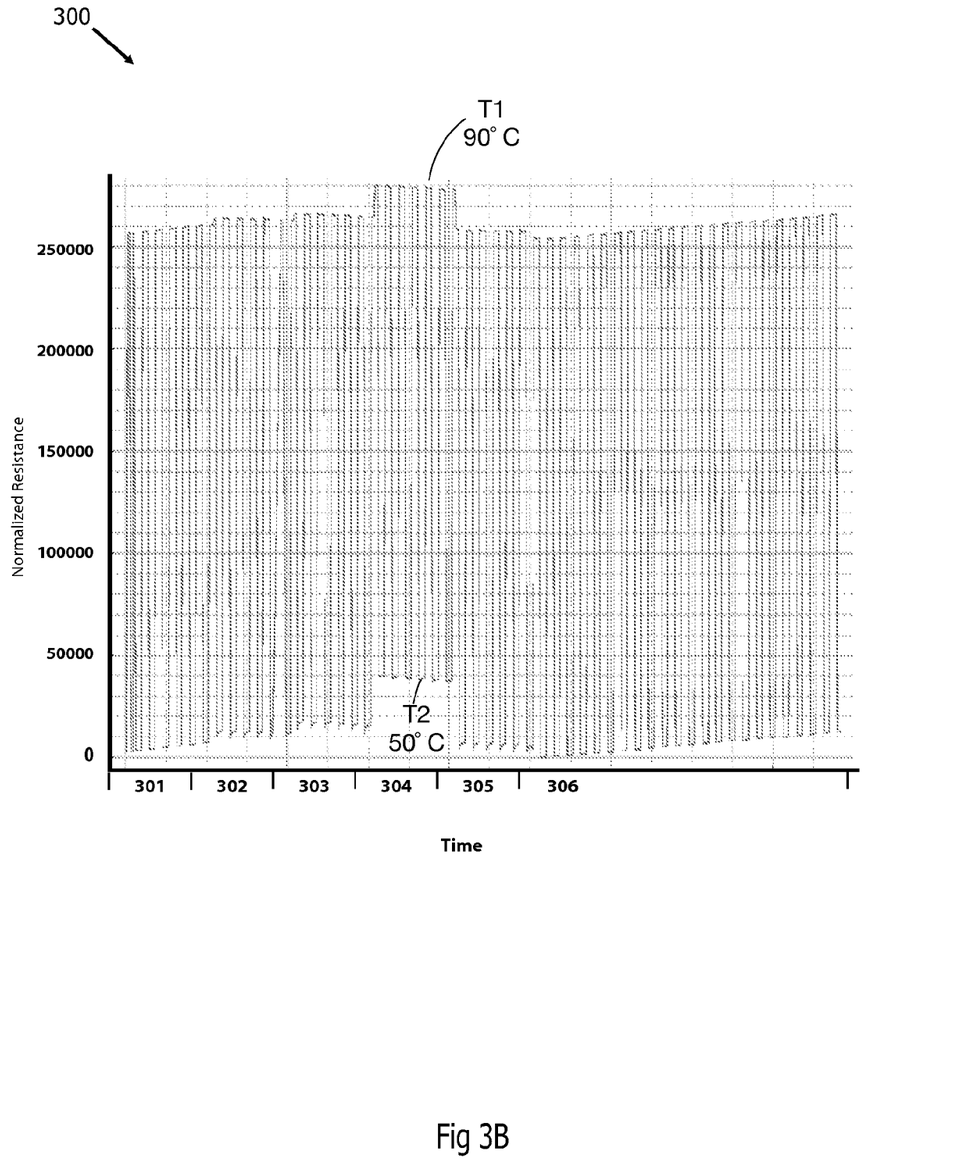
FIG. 3B shows a graph corresponding to measurements of a gas sensor over a period of time, according to an embodiment of the present application.

FIG. 3B shows a graph corresponding to measurements of a gas sensor over a period of time, according to an embodiment of the present application. Like FIG. 3A, a gas sensor may be exposed to the varying mixed atmospheres shown in Table 1. Instead of operating the gas sensor at a constant temperature, however, the sensor is operated at two different temperatures (for example, 50° C. and 90° C. as used when generating data for FIG. 3B). The gas sensor may be operated for a first period of time at the first temperature and for a second period of time at the second temperature.

As the gas sensor temperature cycles, the normalized resistance of the gas sensor may also cycle. For example, the gas sensor may have a greater normalized resistance at a higher temperature than at a lower temperature. It may be useful to measure the resistance of the gas sensor at the ends of the first and second periods of time. For example, it may take a certain amount of time for the temperature of the gas sensor to stabilize, or it may take a certain amount of time for other equilibriums to be achieved. By measuring at the ends of such periods of times, more accurate signal values may be obtained from the gas sensor. In some cases it may be useful to measure the change in the sensor signal over time and to use this rate of change as a signal.

According to the following assumptions and equations, the data from FIG. 3B may be used to reduce undesirable influences or anomalies when measuring concentration information for a target gas. As can be seen in FIG. 3B, the gas sensor may be relatively responsive to a change in temperature. For example, as shown in FIG. 3B, the normalized resistance of the gas sensor may be ~25× greater at 90° C. (T2) than at 50° C. (T1) for the same gas concentration.

As may or may not be evident in FIG. 3B, the response time or rate of the gas sensor to adverse influences, such as the presence of an interfering gas or drift, may be slower or faster than the response time to the target gas. These differences may be used to select the lengths of the cycle times and cycle temperatures in order to extract concentration information for the target gas from interfering information. For example, it may be useful to select cycle times that are (a) long enough to allow the target gas to reach equilibrium with the sensor, and (b) too short for interfering influences to significantly affect the sensor, the interfering factors (including the presence of an interfering gas) can be effectively removed.

In view of these assumptions and techniques, EQS. 1-4 may be derived. First, it may be assumed that the resistance of the gas sensor at temperatures T1 and T2 is due to concentrations for both an interfering gas and a desired gas, for example oxygen and hydrogen:

$$R(T1) = R_{O2}(T1) + R_{H2}(T1) \quad \text{EQ. 1}$$

$$R(T2) = R_{O2}(T2) + R_{H2}(T2) \quad \text{EQ. 2}$$

Due to the relatively long time period required for oxygen to diffuse into the sensor for short time intervals, it may be assumed that:

$$R_{O2}(T1) \approx R_{O2}(T2) \quad \text{EQ. 3}$$

By solving EQS. 1-3, the following equation may be derived:

$$R(T2) - R(T1) = R_{H2}(T2) - R_{H2}(T1) \quad \text{EQ. 4}$$

Turning to FIG. 2, the following calibration equations may be derived:

$$R_{H2}(T1) = g(T1) * \sqrt{H_2} + RO_H(T1) \quad \text{EQ. 5}$$

$$R_{H2}(T2) = g(T2) * \sqrt{H_2} + RO_{H2}(T2) \quad \text{EQ. 6}$$

By solving EQS. 5 and 6, the following may be derived:

$$\sqrt{H_2} = \frac{[R_{H2}(T2) - R_{H2}(T1)] - [RO_{H2}(T2) - RO_{H2}(T1)]}{[g(T2) - g(T1)]} \quad \text{EQ. 7}$$

Lastly, by solving EQS. 4 and 7, one may get:

$$\sqrt{H_2} = \frac{[R(T2) - R(T1)] - [RO_{H2}(T2) - RO_{H2}(T1)]}{[g(T2) - g(T1)]} \quad \text{EQ. 8}$$

Thus, concentration information for $H_2$ may be calculated according to the measured resistance of the gas sensor at T1 and T2. Further information may also be supplied by the calibration relationships 210 and 220. By using the data from FIG. 3B and EQ. 8, the graph 320 in FIG. 3C may be plotted. By using the dual-temperature technique, substantially accurate $H_2$ concentration information measurements may be obtained.

Figure 3C:
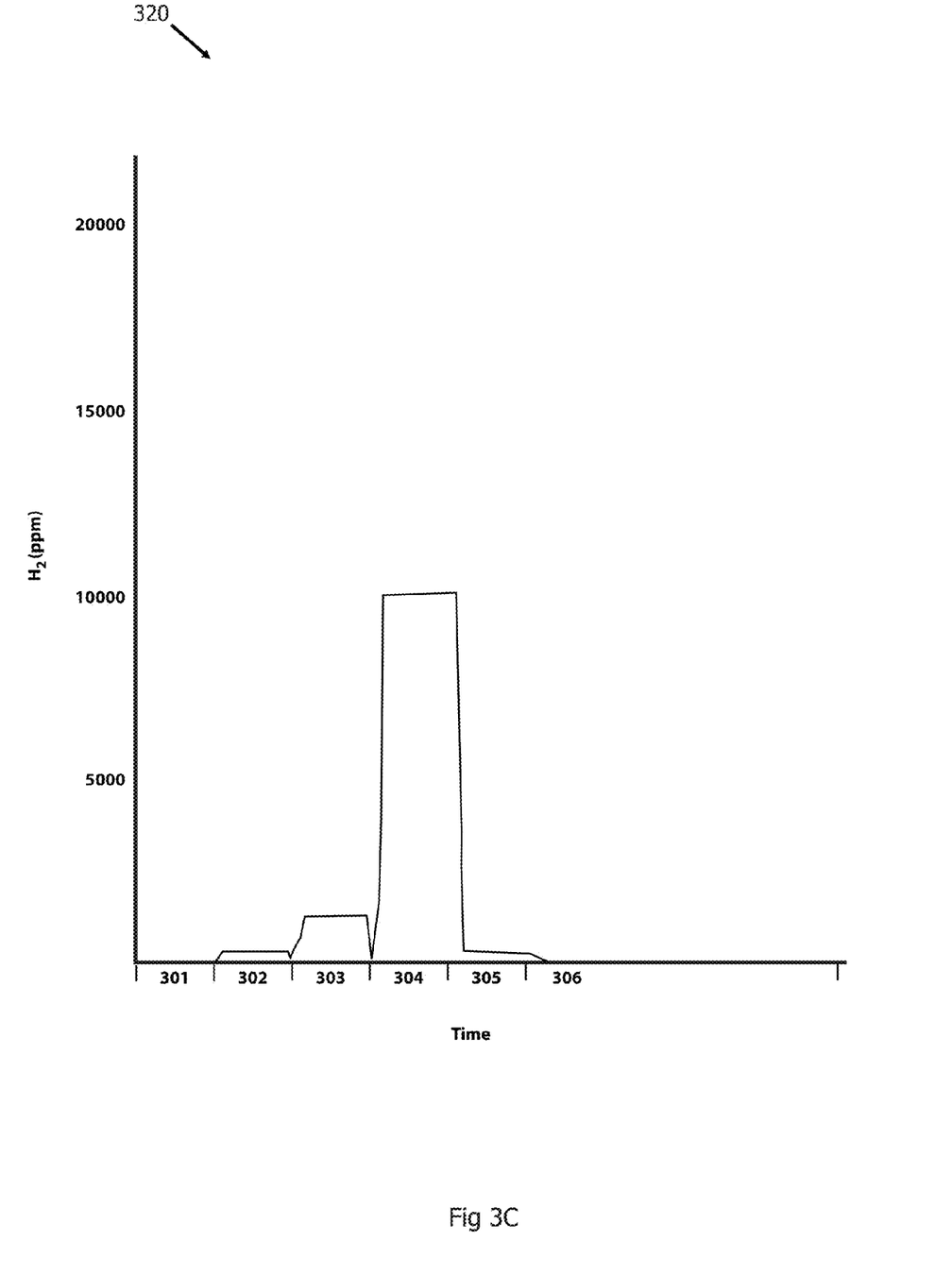
FIG. 3C shows a graph corresponding to concentration information for $H_2$ as calculated by information from a gas sensing system over a period of time, according to an embodiment of the present application.
Figure 3D:
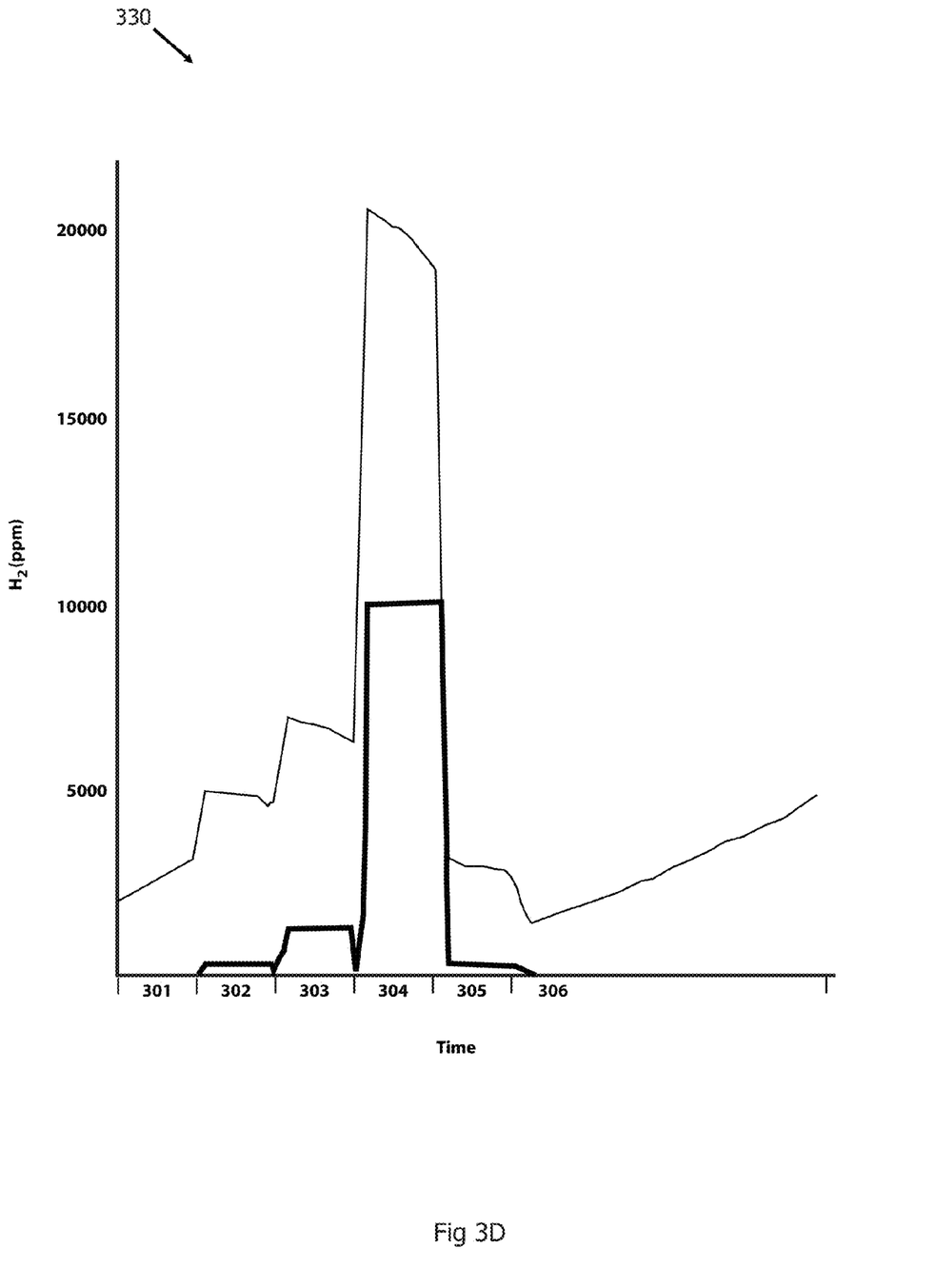
FIG. 3D shows a graph illustrating a comparison of techniques for calculating concentration information for $H_2$, according to an embodiment of the present application.

The disparity between the single-temperature approach and the dual-temperature approach is illustrated in FIG. 3D, which shows the data from FIGS. 3A and 3C together. The data from FIG. 3C is shown with a bold line while the data from FIG. 3A is shown with a thin line. Many of the aforementioned anomalies have been substantially reduced by using the dual-temperature approach. For example, during segments 301 and 306 when $H_2$ is absent from the mixed atmosphere, the calculated $H_2$ concentration information is zero. As another example, segments 302, 303, 304, and 305, the $H_2$ concentration information is accurately calculated to be approximately 300 ppm, 1,000 ppm, 10,000 ppm, and 300 ppm respectively. As another example, the problem of tailing off has been substantially reduced or eliminated.

The principles and techniques shown in FIGS. 1-3 and discussed above may be further developed. For example, it may be useful to add additional cycles, such as cycles at additional temperatures. As another example, one or more additional sensing units may be implemented as part of a gas sensing system. Such an additional sensing unit(s) may be used according to techniques described in conjunction with FIGS. 5-6. As another example, additional processing techniques may be used to improve the accuracy of $H_2$ concentration information calculations. For example, certain adverse influencing factors may be more pronounced at one temperature as compared to another temperature. If the nature of such differences can be predicted in advance of sensing operations, a processor may be able to account for such differences to further improve the accuracy of concentration information measurements.

In addition to temperature cycling, differentiation techniques may be implemented by changing other states besides temperature. For example, biasing voltages for a gas sensor may be adjusted to two or more values. As another example, the pressure of the target environment may be adjusted to two or more different pressures. As yet another example, multiple system aspects (for example, gas sensor temperature, gas sensor biasing voltage, and/or target environment pressure) may be adjusted from one state to the next.

Figure 5:
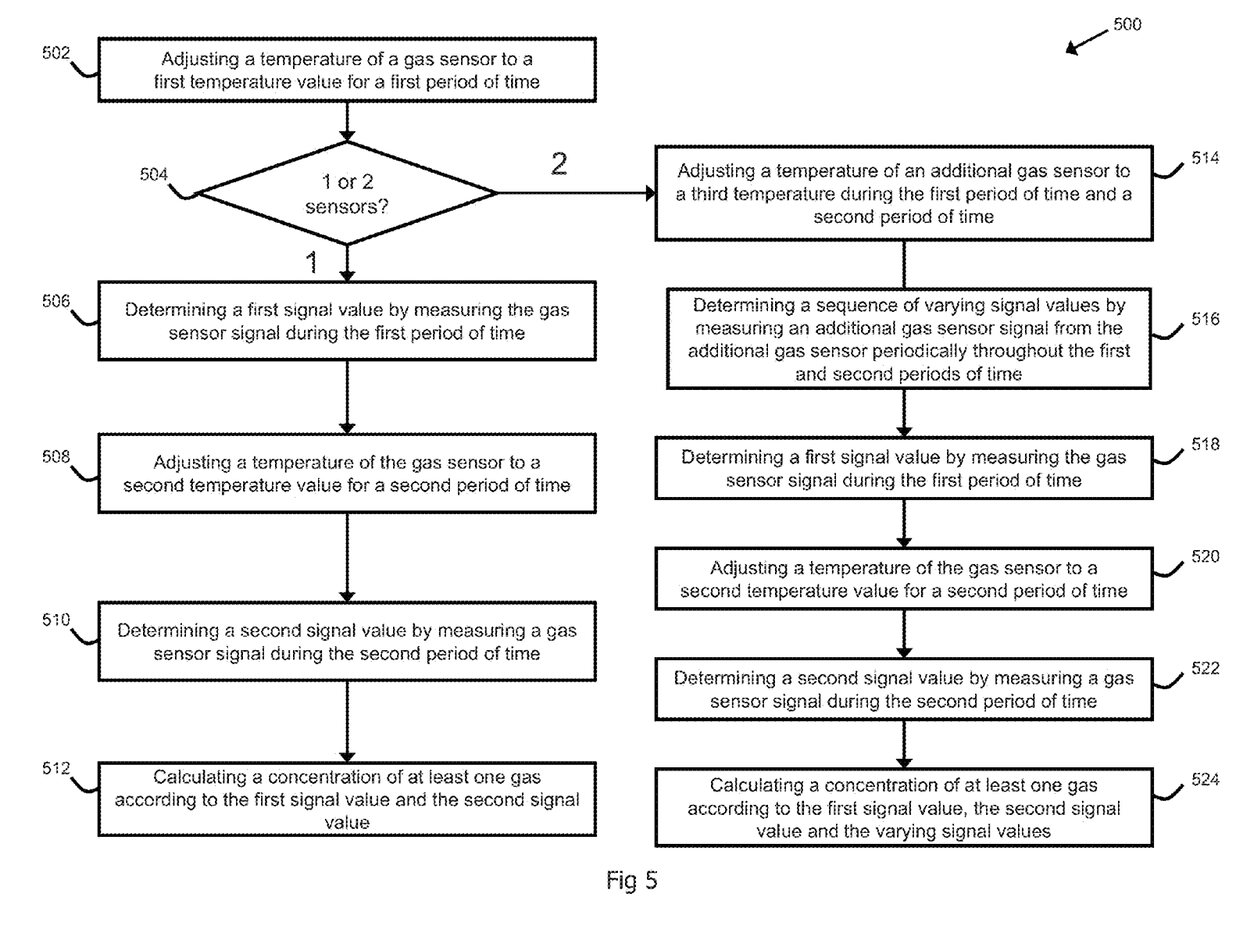
FIG. 5 shows a flowchart for a method of detecting concentration information for a gas, according to an embodiment of the present application.

Turning now to FIG. 5, a flowchart 500 for a method of detecting concentration information of a gas is illustrated, according to an embodiment of the present application. The steps of the flowchart 500 may be performable, for example, by a system, such as system 100. Furthermore, the steps of the flowchart 500 may be performable in a different order, concurrently, in parallel, or some steps may be omitted according to design and/or preferences. For example, steps 514 and/or 504 may be performed before step 502.

At step 502, a temperature of a gas sensor (for example, gas sensor 116) is adjusted to a first temperature value for a first period of time. The first temperature value may be approximately 50° C. As may be applicable to this step and subsequent steps, the temperature of the gas sensor may be adjusted by a processor (for example, processor 120) in closed-loop control of a heater (for example heater 112) through a temperature sensor (for example 114).

At step 504, it is determined whether the system has one or two gas sensors. If there is only one gas sensor, the flowchart proceeds to step 506. Note, step 504 is shown simply to illustrate that there are techniques that involve the use of two gas sensors. If two gas sensors are present, then certain steps may be added or adjusted as described below. Step 504 may, therefore, be performed before step 502.

At step 506, a first signal value is determined by measuring a gas sensor signal from the gas sensor during the first period of time. For example, the first signal value may be measured at approximately the end of the first period of time. Such a technique may be useful if the first period of time is selected according to how long it takes for the gas sensor to stabilize in response to the change in temperature. In this manner, the first signal value may be measured after the gas sensor has substantially stabilized.

At step 508, the temperature of the gas sensor is adjusted to a second temperature value for a second period of time. The second temperature value may be approximately 90° C. At step 510, a second signal value is determined by measuring the gas sensor signal from the gas sensor during the second period of time. For example, the second signal value may be measured at approximately the end of the second period of time. As discussed above, such a technique may be utilized to take the measurement after the gas sensor has stabilized.

At step 512, concentration information for at least one gas is calculated according to the first signal value and the second signal value. This calculation may also be made according to a first calibration relationship (for example, relationship 210) and a second calibration relationship (for example, relationship 220).

Going back to step 504, if there is an additional gas sensor, then the flowchart proceeds to step 514. Again, step 504 is shown to simply illustrate that there are techniques that involve the use of two sensors. One of the advantages of using two gas sensors may result from a potential problem with single-sensor systems as illustrated in FIG. 4.

Figure 4:
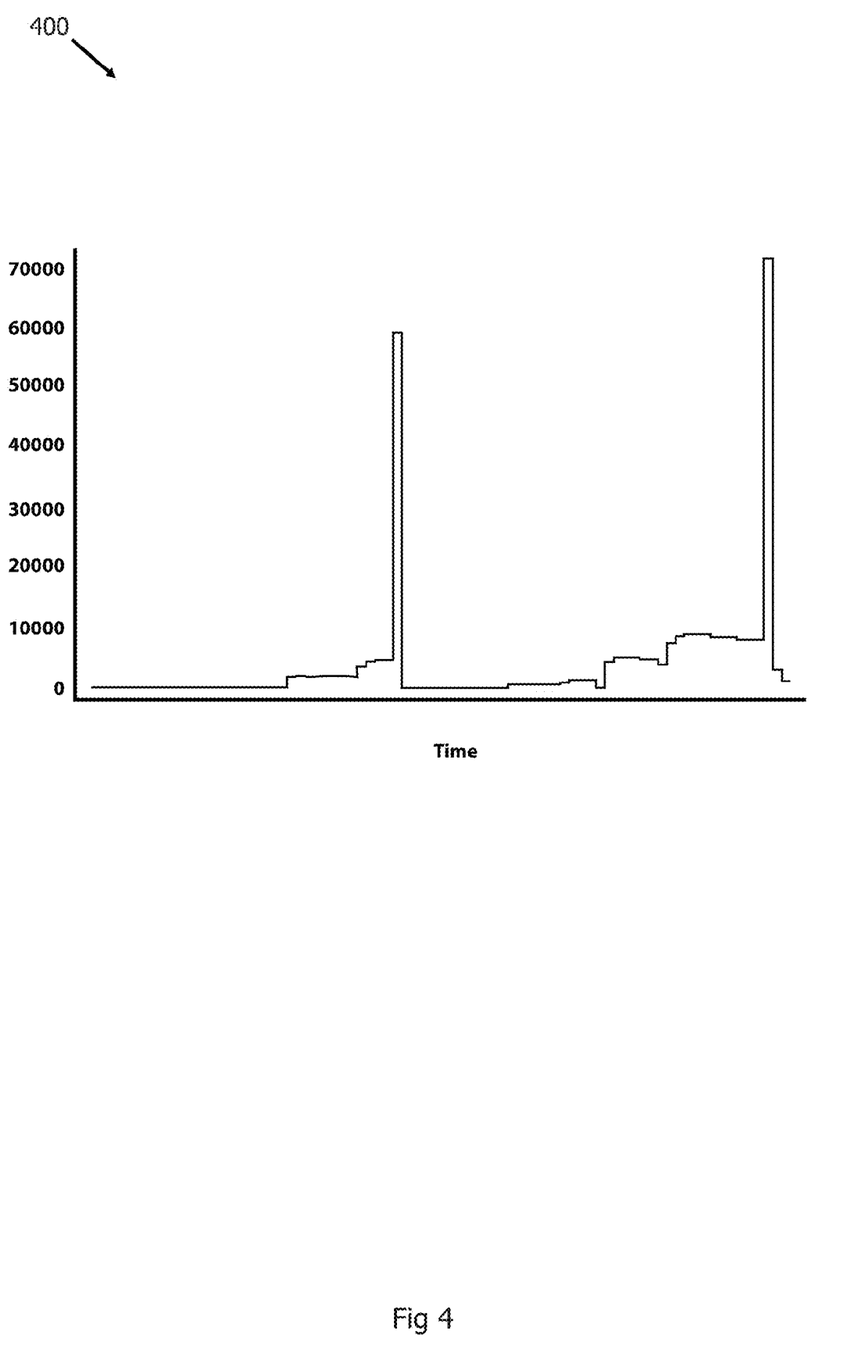
FIG. 4 shows measurements of a gas sensor over a period of time, according to an embodiment of the present application.

FIG. 4 shows a graph 400 depicting measurements of a gas sensor over a period of time. As the graph 400 shows, there are two spikes in the $H_2$ concentration information measurements. These spikes may result from a situation where concentration information for $H_2$ changes relatively rapidly during the first period of time and/or the second period of time. Specifically, if concentration for $H_2$ is not relatively stable when both the first and second signal values are determined, then a spike or artifact may be generated according to EQ. 8.

There may be various solutions to reducing the impact of such artifacts. One solution may be to filter the resulting concentration information with, for example, a low-pass filter. If the spikes have a high frequency (are short in duration) then they may be filtered. Another solution may be to remove the spikes if a threshold is exceeded. Another solution may be to compare the spiking data to previously acquired data and compare it for anomalies or impossibilities/improbabilities.

Another solution may be to use one or more additional gas sensing units. In such a solution, data from the additional gas sensor may be combined with the data from the original gas sensor. For example, the additional gas sensor may operate at a substantially constant temperature throughout sensing operations. One such technique would be to take more frequent periodic measurements throughout the sensing operations from the additional gas sensor. This could provide additional varying signal values that could be combined with the data from the original gas sensor. Various algorithmic or mathematic approaches could be used to combine data from the original gas sensor and the additional gas sensor. In one such approach, it may be possible to effectively recalibrate the additional gas sensor periodically by using relatively accurate measurements according to the dual-temperature gas sensing techniques. In another approach, it may be possible to operate any additional sensors out of phase from the original sensor.

In another approach, additional sensors with different materials or compositions may be used. Such sensors may have differing response characteristics to a target gas or interferences. By operating these sensors at two or more conditions (for example, different temperatures that may be controlled by the processor) additional signals can be obtained. For example one such sensor could contain an alloy of 85% PD and 15% Ni and a second such sensor could contain 100% Pd.

When multiple sensors are used, it may be possible to calibrate one or more additional sensors by using techniques similar to those discussed in conjunction with FIG. 2. Thus, one or more additional sensors may be calibrated at two or more temperatures.

In order to implement such multi-sensor solutions, the flowchart in FIG. 5 may proceed to step 514. At this step, the temperature of the additional gas sensor is adjusted to a third temperature value during both the first period of time and the second period of time. Subsequently, at step 516, a sequence of varying signal values may be determined by measuring a signal from the additional gas sensor periodically throughout the first period of time and the second period of time. Steps 518, 520, and 522 may be performed and may be similar to steps 506, 508, and 510, respectively. Step 516 may be performed concurrently or in parallel with other steps, such as step 502, 518, 520, or 522.

At step 524, a concentration information for the at least one gas is calculated according to the first signal value, the second signal value, and the varying signal values from the additional gas sensor.

Figure 6:
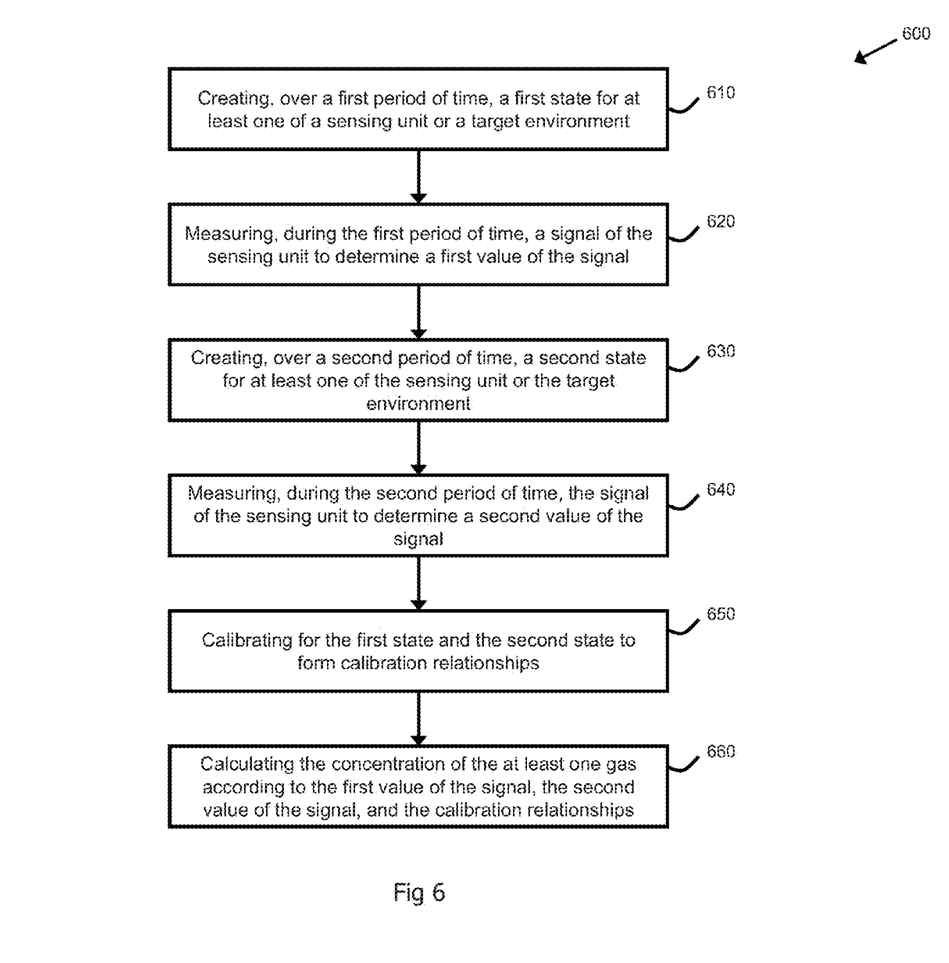
FIG. 6 shows a flowchart for a method of detecting concentration information for a gas, according to an embodiment of the present application.

Turning now to FIG. 6, a flowchart 600 for a method of detecting concentration information for a gas is illustrated, according to an embodiment of the present application. The steps of the flowchart 600 may be performable, for example, by a system, such as system 100. Furthermore, the steps of the flowchart 600 may be performable in a different order, concurrently, in parallel, or some steps may be omitted according to design and/or preferences.

At step 610, a first state is created over a first period of time for at least one of a sensing unit or a target environment. A first state may be created, for example, by adjusting the temperature of a gas sensor, the bias voltage of the gas sensor, and/or the pressure of the target environment.

At step 620, a signal of the sensing unit is measured during the first period of time to determine a first value of the signal. For example, the first signal value may be measured at approximately the end of the first period of time. Such a technique may be useful if the first period of time is selected according to how long it takes for the gas sensor or target environment to stabilize in response to a change to the first state. In this manner, the first signal value may be measured after the gas sensor or target environment have substantially stabilized.

At step 630, a second state different from the first state is created over a second period of time for at least one of the sensing unit or the target environment. Like step 610, the second state may be created, for example, by adjusting the temperature of the gas sensor, the bias voltage of the gas sensor, and/or the pressure of the target environment.

At step 640, the signal of the sensing unit is measured during the second period of time to determine a second value of the signal. Like step 620, the second signal value may be measured at approximately the end of the second period of time. Such a technique may be useful if the second period of time is selected according to how long it takes for the gas sensor or target environment to stabilize in response to a change to the second state. In this manner, the second signal value may be measured after the gas sensor or target environment have substantially stabilized.

At step 650, calibration relationships are formed by calibrating the sensing unit at the first state and the second state. In a manner similar to that discussed above in conjunction with FIGS. 2 and 5, the sensing unit can be calibrated at the first state and the second state to form corresponding calibration relationships.

At step 660, concentration information for the at least one gas is calculated according to the first value of the signal, the second value of the signal, or the calibration relationships. Similar to the descriptions above, the calculated concentration information may substantially correspond to only one of the gasses (for example, $H_2$) in a target environment with multiple gasses (for example, $H_2$ and $O_2$).

One or more of the steps of the foregoing methods or flowcharts may be implemented with one or more computer-readable media, which may be any available media that can be accessed by a processor (for example, microprocessor, microcontroller, digital signal processor, etc.) or general purpose or special purpose computer. By way of example, and not limitation, such computer-readable media may include RAM, ROM, EEPROM, CD-ROM or other optical disk storage, magnetic disk storage or other magnetic storage devices, or any other medium which can be used to carry or store desired program code information in the form of computer-executable instructions or data structures and which can be accessed by a general purpose or special purpose computer. The computer-executable instructions comprise, for example, instructions and data which cause a general purpose computer, special purpose computer, or special purpose processing device to perform a certain function or group of functions, such as the methods or portions thereof described herein.

While the application has been described with reference to certain embodiments, it will be understood by those skilled in the art that various changes may be made and equivalents may be substituted without departing from the scope of the application. For example, the disclosed techniques may be applicable to detection of target gasses such as $O_2$ or CO or with other types of gas sensors, such as nanosensors. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

The invention claimed is:

1. A system comprising:
a sensing unit including:
   a gas sensor configured to generate a gas sensor signal in response to a presence of at least one gas, and
   a heater configured to adjust a temperature of the sensor; and
at least one processor adapted to:
   control the heater to adjust the temperature of the sensor to a first temperature at a first time;
   determine a first signal value by measuring the gas sensor signal at the first time;
   control the heater to adjust the temperature of the sensor to a second temperature at a second time, wherein the first temperature and the second temperature are different;
   determine a second signal value by measuring the gas sensor signal at the second time; and
   calculate concentration information for the at least one gas based at least in part on:
      the first signal value and a relationship between resistance of the gas sensor versus a concentration of $H_2$ when the gas sensor is at the first temperature; and
      the second signal value and a relationship between resistance of the gas sensor versus a concentration of $H_2$ when the gas sensor is at the second temperature.

2. The system of claim 1, wherein:
the gas sensor is configured to generate the gas sensor signal in response to a presence of a first gas and a second gas; and
the concentration information for the at least one gas includes concentration information for the first gas and does not substantially include concentration information for the second gas.

3. The system of claim 2, wherein the first gas is $H_2$ and the second gas is $O_2$.

4. The system of claim 1, wherein the at least one processor is further adapted to:
control the heater to adjust the temperature of the sensor to a third temperature at a third time;
determine a third signal value by measuring the gas sensor signal at the third time; and
calculate concentration information for the at least one gas based at least in part on:
   the first signal value and the first calibration relationship of the gas sensor at the first temperature;

the second signal value and the second calibration relationship of the gas sensor at the second temperature; and the third signal value and a third calibration relationship of the gas sensor at the third temperature.

5. The system of claim 1, further comprising:

an additional sensing unit including:

a gas sensor configured to generate an additional gas sensor signal in response to the presence of the at least one gas, and a heater configured to adjust a temperature of the additional sensor; and wherein the at least one processor is adapted to:

control the heater of the additional sensing unit to adjust the temperature of the additional gas sensor to an additional temperature at the first time and the second time;

determine a sequence of varying signal values by periodically measuring the additional gas sensor signal; and determine concentration information for the at least one gas based at least in part on the first signal value, the second signal value, and the varying signal values.

6. The system of claim 5, wherein the at least one processor is adapted to calibrate the gas sensor using the varying signal values.

7. The system of claim 5, wherein the additional temperature and the first temperature are substantially the same.

8. The system of claim 1, wherein:

the first signal value comprises a rate of change of the gas sensor signal at the first time; and the second signal value comprises a rate of change of the gas sensor signal at the second time.

9. A method comprising:

exposing a gas sensor to at least one gas;

adjusting a temperature of the gas sensor to a first temperature at a first time;

determining a first signal value by measuring a gas sensor signal from the gas sensor at the first time;

adjusting the temperature of the gas sensor to a second temperature at a second time;

determining a second signal value by measuring the gas sensor signal at the second time;

calculating concentration information for the at least one gas based at least in part on:

the first signal value and a relationship between resistance of the gas sensor versus a concentration of $H_2$ when the gas sensor is at the first temperature; and the second signal value and relationship between resistance of the gas sensor versus a concentration of $H_2$ when the gas sensor is at the second temperature; and wherein the first temperature is different than the second temperature.

10. The method of claim 9, wherein:

the gas sensor is configured to generate the gas sensor signal in response to a presence of a first gas and a second gas; and the concentration information for the at least one gas includes concentration information for the first gas and does not substantially include concentration information for the second gas.

11. The method of claim 10, wherein the first gas is $H_2$ and the second gas is $O_2$.

12. The method of claim 9, further comprising:

adjusting the temperature of the sensor to a third temperature at a third time;

determining a third signal value by measuring the gas sensor signal at the third time; and wherein said calculating concentration information for at least one gas further comprises calculating concentration information for the at least one gas based at least in part on:

the first signal value and the first calibration relationship of the gas sensor at the first temperature;

the second signal value and the second calibration relationship of the gas sensor at the second temperature; and the third signal value and a third calibration relationship of the gas sensor at the third temperature.

13. The method of claim 9, further comprising:

controlling a heater associated with an additional gas sensor to adjust the temperature of the additional gas sensor to an additional temperature at the first time and the second time:

determining a sequence of varying signal values by periodically measuring an additional gas sensor signal of a gas sensor of the additional sensing unit; and determining concentration information for the at least one gas based at least in part on the first signal value, the second signal value, and the varying signal values.

14. The method of claim 13, further comprising:

calibrating the gas sensor using the varying signal values.

15. The method of claim 13, wherein the additional temperature and the first temperature are substantially the same.

16. The method of claim 9, wherein:

the first signal value comprises a rate of change of the gas sensor signal at the first time; and the second signal value comprises a rate of change of the gas sensor signal at the second time.

17. A method comprising:

creating, at a first time, a first state for a target environment, the target environment including the presence of at least one gas;

measuring, at the first time, a signal of a gas sensor in the target environment to determine a first value of the signal;

creating, at a second time, a second state for the target environment;

measuring, at the second time, the signal of the gas sensor to determine a second value of the signal;

calculating concentration information for the at least one gas in the target environment based at least in part on the first value and the second value of the signal; and wherein:

the first state is different than the second state;

the first state includes at least one of a first pressure of the target environment or a first bias voltage of the gas sensor; and the second state includes at least one of a second pressure of the target environment or a second bias voltage of the gas sensor.

18. The method of claim 17, wherein:

the first state comprises the first pressure of the target environment; and the second state comprises the second pressure of the target environment.

19. The method of claim 17, wherein:

the first state comprises the first bias voltage of the gas sensor; and the second state comprises the second bias voltage of the gas sensor.

20. The method of claim 17, wherein said calculating concentration information for at least one gas in the target environment based at least in part on the first value and the second value of the signal further comprises:
- calculating concentration information for the at least one gas in the target environment based at least in part on the first value of the signal, the second value of the signal, and a plurality of calibration relationships of the gas sensor at the first state and the second state.

21. The method of claim 17, further comprising:
- generating the signal of the gas sensor in response to a presence of a first gas and a second gas; and
- wherein the concentration information for the at least one gas includes concentration information for the first gas and does not substantially include concentration information for the second gas.

22. The method of claim 21, wherein the first gas is $H_2$ and the second gas is $O_2$.

23. The method of claim 17, further comprising:
- creating, at a third time, a third state for the target environment;
- measuring, at the third time, the signal of the gas sensor to determine a third value of the signal; and
- calculating concentration information for at least one gas in the target environment based at least in part on the first value of the signal, the second value of the signal, and the third value of the signal.

24. The method of claim 17, wherein:
- the a first value of the signal comprises a rate of change of the signal of the gas sensor at the first time; and
- the a second value of the signal comprises a rate of change of the signal of the gas sensor at the second time.

* * * * *